(12) United States Patent
Dunki-Jacobs

(10) Patent No.: US 7,589,316 B2
(45) Date of Patent: Sep. 15, 2009

(54) SCANNING BEAM IMAGING WITH ADJUSTABLE DETECTOR SENSITIVITY OR GAIN

(75) Inventor: Robert J. Dunki-Jacobs, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 6 days.

(21) Appl. No.: 11/624,238

(22) Filed: Jan. 18, 2007

(65) Prior Publication Data
US 2008/0173803 A1 Jul. 24, 2008

(51) Int. Cl.
*H03F 3/08* (2006.01)
*A61B 1/04* (2006.01)

(52) U.S. Cl. ............... 250/235; 250/214 A; 250/214 C; 600/109; 600/160; 356/608

(58) Field of Classification Search ............. 250/214 A, 250/214 C, 234, 235, 559.22; 600/101, 109, 600/160, 476; 356/600, 601, 602, 608; 359/212, 359/213, 214, 215
See application file for complete search history.

(56) References Cited

U.S. PATENT DOCUMENTS

| | | | |
|---|---|---|---|
| 3,758,199 A | 9/1973 | Thaxter | |
| 3,959,582 A | 5/1976 | Law et al. | |
| 4,082,635 A | 4/1978 | Fritz et al. | |
| 4,141,362 A | 2/1979 | Wurster | |
| 4,313,431 A | 2/1982 | Frank | |
| 4,379,039 A | 4/1983 | Fujimoto et al. | |
| 4,403,273 A | 9/1983 | Nishioka | |
| 4,409,477 A | 10/1983 | Carl | |
| 4,421,382 A | 12/1983 | Doi et al. | |
| 4,524,761 A | 6/1985 | Hattori et al. | |
| 4,527,552 A | 7/1985 | Hattori | |
| 4,573,465 A | 3/1986 | Sugiyama et al. | |
| 4,576,999 A | 3/1986 | Eckberg | |
| 4,597,380 A | 7/1986 | Raif et al. | |
| 4,643,967 A | 2/1987 | Bryant | |
| 4,676,231 A | 6/1987 | Hisazumi et al. | |
| 4,760,840 A | 8/1988 | Fournier, Jr. et al. | |
| 4,803,550 A * | 2/1989 | Yabe et al. ............... | 348/68 |

(Continued)

FOREIGN PATENT DOCUMENTS

DE 3837248 5/1990

(Continued)

OTHER PUBLICATIONS

Kiang, M-H et al., "Surface-Micromachined Electrostatic-Comb Driven Scanning Micromirrors for Barcode Scanners" (date of first publication unknown).

(Continued)

*Primary Examiner*—Stephen Yam
(74) *Attorney, Agent, or Firm*—Victor Moreno (57) ABSTRACT

A scanning beam assembly comprising: a beam generator to generate a beam of radiation, an oscillating reflector configured to deflect the beam at varying angles of excursion to yield a scanned beam that scans a field of view, an optical detector that detects light reflected from the field of view, the detector including at least one of an adjustable gain and adjustable sensitivity, and a controller programmable to control the gain and/or sensitivity of the detector.

19 Claims, 5 Drawing Sheets

U.S. PATENT DOCUMENTS

| | | |
|---|---|---|
| 4,872,458 A | 10/1989 | Kanehira et al. |
| 4,902,083 A | 2/1990 | Wells |
| 4,902,115 A | 2/1990 | Takahashi |
| 4,934,773 A | 6/1990 | Becker |
| 4,938,205 A | 7/1990 | Nudelman |
| 5,003,300 A | 3/1991 | Wells |
| 5,023,905 A | 6/1991 | Wells et al. |
| 5,048,077 A | 9/1991 | Wells et al. |
| 5,074,860 A | 12/1991 | Gregory et al. |
| 5,078,150 A | 1/1992 | Hara et al. |
| 5,163,936 A | 11/1992 | Black et al. |
| 5,163,945 A | 11/1992 | Ortiz et al. |
| 5,172,685 A | 12/1992 | Nudelman |
| 5,192,288 A | 3/1993 | Thompson et al. |
| 5,200,819 A | 4/1993 | Nudelman et al. |
| 5,200,838 A | 4/1993 | Nudelman et al. |
| 5,207,670 A | 5/1993 | Sinofsky |
| 5,218,195 A | 6/1993 | Hakamata |
| 5,251,025 A | 10/1993 | Cooper et al. |
| 5,251,613 A | 10/1993 | Adair |
| 5,269,289 A * | 12/1993 | Takehana et al. ............ 600/109 |
| 5,318,024 A | 6/1994 | Kittrell et al. |
| 5,334,991 A | 8/1994 | Wells et al. |
| 5,368,015 A | 11/1994 | Wilk |
| 5,370,643 A | 12/1994 | Krivoshlykov et al. |
| 5,387,197 A | 2/1995 | Smith et al. |
| 5,393,647 A | 2/1995 | Neukermans et al. |
| 5,436,655 A | 7/1995 | Hiyama et al. |
| 5,467,104 A | 11/1995 | Furness, III et al. |
| 5,488,862 A | 2/1996 | Neukermans et al. |
| 5,531,740 A | 7/1996 | Black |
| 5,545,211 A | 8/1996 | An et al. |
| 5,552,452 A | 9/1996 | Khadem et al. |
| 5,557,444 A | 9/1996 | Melville et al. |
| 5,590,660 A | 1/1997 | MacAulay et al. |
| 5,596,339 A | 1/1997 | Furness, III et al. |
| 5,608,451 A * | 3/1997 | Konno et al. .................. 348/69 |
| 5,629,790 A | 5/1997 | Neukermans et al. |
| 5,648,618 A | 7/1997 | Neukermans et al. |
| 5,649,952 A | 7/1997 | Lam |
| 5,657,165 A | 8/1997 | Karpman et al. |
| 5,658,710 A | 8/1997 | Neukermans |
| 5,659,327 A | 8/1997 | Furness, III et al. |
| 5,694,237 A | 12/1997 | Melville |
| 5,701,132 A | 12/1997 | Kollin et al. |
| 5,713,891 A | 2/1998 | Poppas |
| 5,728,121 A | 3/1998 | Bimbo et al. |
| 5,735,792 A | 4/1998 | Vanden Hoek et al. |
| 5,742,419 A | 4/1998 | Dickensheets et al. |
| 5,742,421 A | 4/1998 | Wells et al. |
| 5,751,465 A | 5/1998 | Melville et al. |
| 5,768,461 A | 6/1998 | Svetkoff et al. |
| 5,797,944 A | 8/1998 | Nobles et al. |
| 5,817,061 A | 10/1998 | Goodwin et al. |
| 5,823,943 A | 10/1998 | Tomioka et al. |
| 5,827,176 A | 10/1998 | Tanaka et al. |
| 5,827,190 A | 10/1998 | Palcic et al. |
| 5,841,553 A | 11/1998 | Neukermans |
| 5,861,549 A | 1/1999 | Neukermans et al. |
| 5,867,297 A | 2/1999 | Kiang et al. |
| 5,895,866 A | 4/1999 | Neukermans et al. |
| 5,903,397 A | 5/1999 | Melville et al. |
| 5,907,425 A | 5/1999 | Dickensheets et al. |
| 5,913,591 A | 6/1999 | Melville |
| 5,947,930 A | 9/1999 | Schwemberger et al. |
| 5,969,465 A | 10/1999 | Neukermans et al. |
| 5,969,871 A | 10/1999 | Tidwell et al. |
| 5,982,528 A | 11/1999 | Melville |
| 5,982,555 A | 11/1999 | Melville et al. |
| 5,993,037 A | 11/1999 | Tomioka et al. |
| 5,995,264 A | 11/1999 | Melville |
| 6,007,208 A | 12/1999 | Dickensheets et al. |
| 6,008,781 A | 12/1999 | Furness, III et al. |
| 6,013,025 A | 1/2000 | Bonne et al. |
| 6,016,440 A | 1/2000 | Simon et al. |
| 6,017,356 A | 1/2000 | Frederick et al. |
| 6,017,603 A | 1/2000 | Tokuda et al. |
| 6,024,744 A | 2/2000 | Kese et al. |
| 6,043,799 A | 3/2000 | Tidwell |
| 6,044,705 A | 4/2000 | Neukermans et al. |
| 6,046,720 A | 4/2000 | Melville et al. |
| 6,049,407 A | 4/2000 | Melville |
| 6,056,721 A | 5/2000 | Shulze |
| 6,057,952 A | 5/2000 | Kubo et al. |
| 6,059,720 A * | 5/2000 | Furusawa et al. ........... 600/160 |
| 6,061,163 A | 5/2000 | Melville |
| 6,064,779 A | 5/2000 | Neukermans et al. |
| 6,069,725 A | 5/2000 | Melville |
| 6,086,528 A | 7/2000 | Adair |
| 6,086,531 A | 7/2000 | Tomioka et al. |
| 6,088,145 A | 7/2000 | Dickensheets et al. |
| 6,097,353 A | 8/2000 | Melville et al. |
| 6,122,394 A | 9/2000 | Neukermans et al. |
| 6,139,175 A | 10/2000 | Tomioka et al. |
| 6,140,979 A | 10/2000 | Gerhard et al. |
| 6,151,167 A | 11/2000 | Melville |
| 6,154,305 A | 11/2000 | Dickensheets et al. |
| 6,154,321 A | 11/2000 | Melville et al. |
| 6,157,352 A | 12/2000 | Kollin et al. |
| 6,166,841 A | 12/2000 | Melville |
| 6,172,789 B1 | 1/2001 | Kino et al. |
| 6,178,346 B1 | 1/2001 | Amundson et al. |
| 6,179,776 B1 | 1/2001 | Adams et al. |
| 6,191,761 B1 | 2/2001 | Melville et al. |
| 6,192,267 B1 | 2/2001 | Scherninski et al. |
| 6,200,595 B1 | 3/2001 | Motoyashiki et al. |
| 6,204,829 B1 | 3/2001 | Tidwell |
| 6,204,832 B1 | 3/2001 | Melville et al. |
| 6,207,392 B1 | 3/2001 | Weiss et al. |
| 6,210,401 B1 | 4/2001 | Lai |
| 6,220,711 B1 | 4/2001 | Melville |
| 6,221,068 B1 | 4/2001 | Fried et al. |
| 6,229,139 B1 | 5/2001 | Neukermans et al. |
| 6,235,017 B1 | 5/2001 | Jegorov et al. |
| 6,243,186 B1 | 6/2001 | Melville |
| 6,245,590 B1 | 6/2001 | Wine et al. |
| 6,256,131 B1 | 7/2001 | Wine et al. |
| 6,257,727 B1 | 7/2001 | Melville |
| 6,272,907 B1 | 8/2001 | Neukermans et al. |
| 6,276,798 B1 | 8/2001 | Gil et al. |
| 6,281,862 B1 | 8/2001 | Tidwell et al. |
| 6,284,185 B1 | 9/2001 | Tokuda et al. |
| 6,285,489 B1 | 9/2001 | Helsel et al. |
| 6,285,505 B1 | 9/2001 | Melville et al. |
| 6,288,816 B1 | 9/2001 | Melville et al. |
| 6,292,287 B1 | 9/2001 | Fujinoki |
| 6,293,911 B1 | 9/2001 | Imaizumi et al. |
| 6,294,239 B1 | 9/2001 | Tokuda et al. |
| 6,294,775 B1 | 9/2001 | Seibel et al. |
| 6,317,103 B1 | 11/2001 | Furness, III et al. |
| 6,323,037 B1 | 11/2001 | Lauto et al. |
| 6,324,007 B1 | 11/2001 | Melville |
| 6,327,493 B1 | 12/2001 | Ozawa et al. |
| 6,331,909 B1 | 12/2001 | Dunfield |
| 6,333,110 B1 | 12/2001 | Barbera-Guillem |
| 6,338,641 B2 | 1/2002 | Nicholls |
| 6,352,344 B2 | 3/2002 | Tidwell |
| 6,353,183 B1 | 3/2002 | Ott et al. |
| 6,362,912 B1 | 3/2002 | Lewis et al. |
| 6,364,829 B1 | 4/2002 | Fulghum |
| 6,369,928 B1 | 4/2002 | Mandella et al. |
| 6,369,953 B2 | 4/2002 | Melville et al. |
| 6,369,954 B1 | 4/2002 | Berge et al. |
| 6,370,406 B1 | 4/2002 | Wach et al. |

| | | | | | |
|---|---|---|---|---|---|
| 6,370,422 B1 | 4/2002 | Richards-Kortum et al. | 6,786,382 B1 | 9/2004 | Hoffman |
| 6,373,995 B1 | 4/2002 | Moore | 6,795,221 B1 | 9/2004 | Urey |
| 6,384,406 B1 | 5/2002 | Wine et al. | 6,802,809 B2 | 10/2004 | Okada |
| 6,388,641 B2 | 5/2002 | Tidwell et al. | 6,803,561 B2 | 10/2004 | Dunfield |
| 6,392,220 B1 | 5/2002 | Slater et al. | 6,821,245 B2 | 11/2004 | Cline et al. |
| 6,396,461 B1 | 5/2002 | Lewis et al. | 6,845,190 B1 | 1/2005 | Smithwick et al. |
| 6,414,779 B1 | 7/2002 | Mandella et al. | 6,856,436 B2 | 2/2005 | Brukilacchio et al. |
| 6,417,502 B1 | 7/2002 | Stoner et al. | 6,856,712 B2 | 2/2005 | Fauver et al. |
| 6,423,956 B1 | 7/2002 | Mandella et al. | 6,879,428 B2 | 4/2005 | Massieu |
| 6,425,900 B1 | 7/2002 | Knodel et al. | 6,888,552 B2 | 5/2005 | Debevec et al. |
| 6,426,013 B1 | 7/2002 | Neukermans et al. | 6,894,823 B2 | 5/2005 | Taylor et al. |
| 6,433,907 B1 | 8/2002 | Lippert et al. | 6,899,675 B2 | 5/2005 | Cline et al. |
| 6,435,637 B1 | 8/2002 | Lyman | 6,902,527 B1 * | 6/2005 | Doguchi et al. .............. 600/109 |
| 6,441,356 B1 | 8/2002 | Mandella et al. | 6,905,057 B2 | 6/2005 | Swayze et al. |
| 6,445,362 B1 | 9/2002 | Tegreene | 6,939,364 B1 | 9/2005 | Soltz et al. |
| 6,447,524 B1 | 9/2002 | Knodel et al. | 6,957,898 B2 | 10/2005 | Yu |
| 6,462,770 B1 | 10/2002 | Cline et al. | 6,967,757 B1 | 11/2005 | Allen et al. |
| 6,464,363 B1 | 10/2002 | Nishioka et al. | 6,974,472 B2 | 12/2005 | Hong et al. |
| 6,467,345 B1 | 10/2002 | Neukermans et al. | 6,975,898 B2 | 12/2005 | Seibel et al. |
| 6,470,124 B1 | 10/2002 | Le Gargasson et al. | 6,976,994 B2 | 12/2005 | Ballou et al. |
| 6,477,403 B1 | 11/2002 | Eguchi et al. | 6,978,921 B2 | 12/2005 | Shelton, IV et al. |
| 6,478,809 B1 | 11/2002 | Brotz | 6,985,271 B2 | 1/2006 | Yazdi et al. |
| 6,485,413 B1 | 11/2002 | Boppart et al. | 6,991,602 B2 | 1/2006 | Nakazawa et al. |
| 6,492,962 B2 | 12/2002 | Melville et al. | 7,005,195 B2 | 2/2006 | Cheng et al. |
| 6,494,578 B1 | 12/2002 | Plummer et al. | 7,009,634 B2 | 3/2006 | Iddan et al. |
| 6,503,196 B1 | 1/2003 | Kehr et al. | 7,013,730 B2 | 3/2006 | Malametz |
| 6,510,338 B1 | 1/2003 | Irion et al. | 7,015,956 B2 | 3/2006 | Luo et al. |
| 6,512,622 B2 | 1/2003 | Wine et al. | 7,018,401 B1 | 3/2006 | Hyodoh et al. |
| 6,513,939 B1 | 2/2003 | Fettig et al. | 7,023,402 B2 | 4/2006 | Lewis et al. |
| 6,515,278 B2 | 2/2003 | Wine et al. | 7,025,777 B2 | 4/2006 | Moore |
| 6,515,781 B2 | 2/2003 | Lewis et al. | 7,033,348 B2 | 4/2006 | Alfano et al. |
| 6,520,972 B2 | 2/2003 | Peters | 7,035,777 B2 | 4/2006 | Araki et al. |
| 6,522,444 B2 | 2/2003 | Mandella et al. | 7,061,450 B2 | 6/2006 | Bright et al. |
| 6,525,310 B2 | 2/2003 | Dunfield | 7,065,301 B2 | 6/2006 | Shastri et al. |
| 6,527,708 B1 | 3/2003 | Nakamura et al. | 7,066,879 B2 | 6/2006 | Fowler et al. |
| 6,529,770 B1 | 3/2003 | Grimblatov | 7,071,594 B1 | 7/2006 | Yan et al. |
| 6,530,698 B1 | 3/2003 | Kuhara et al. | 7,071,931 B2 | 7/2006 | Tegreene et al. |
| 6,535,183 B2 | 3/2003 | Melville et al. | 7,078,378 B1 | 7/2006 | Owen et al. |
| 6,535,325 B2 | 3/2003 | Helsel et al. | 7,108,656 B2 | 9/2006 | Fujikawa et al. |
| 6,537,211 B1 | 3/2003 | Wang et al. | 7,112,302 B2 | 9/2006 | Yoshimi et al. |
| 6,538,625 B2 | 3/2003 | Tidwell et al. | 7,126,903 B2 | 10/2006 | Feenstra et al. |
| 6,545,260 B1 | 4/2003 | Katashiro et al. | 7,189,961 B2 | 3/2007 | Johnston et al. |
| 6,560,028 B2 | 5/2003 | Melville et al. | 7,190,329 B2 | 3/2007 | Lewis et al. |
| 6,563,105 B2 | 5/2003 | Seibel et al. | 7,232,071 B2 | 6/2007 | Lewis et al. |
| 6,563,106 B1 | 5/2003 | Bowers et al. | 7,271,383 B2 | 9/2007 | Chee |
| 6,572,606 B2 | 6/2003 | Kliewer et al. | 7,391,013 B2 | 6/2008 | Johnston et al. |
| 6,583,117 B2 | 6/2003 | Owen et al. | 2001/0055462 A1 | 12/2001 | Seibel |
| 6,583,772 B1 | 6/2003 | Lewis et al. | 2002/0015724 A1 | 2/2002 | Yang et al. |
| 6,585,642 B2 | 7/2003 | Christopher | 2002/0024495 A1 | 2/2002 | Lippert et al. |
| 6,603,552 B1 | 8/2003 | Cline et al. | 2002/0050956 A1 | 5/2002 | Gerhard et al. |
| 6,608,297 B2 | 8/2003 | Neukermans et al. | 2002/0075284 A1 | 6/2002 | Rabb, III |
| 6,639,570 B2 | 10/2003 | Furness, III et al. | 2002/0088925 A1 | 7/2002 | Nestorovic et al. |
| 6,639,719 B2 | 10/2003 | Tegreene et al. | 2002/0115922 A1 | 8/2002 | Waner et al. |
| 6,650,877 B1 | 11/2003 | Tarbouriech et al. | 2002/0141026 A1 | 10/2002 | Wiklof et al. |
| 6,653,621 B2 | 11/2003 | Wine et al. | 2002/0158814 A1 | 10/2002 | Bright et al. |
| 6,654,158 B2 | 11/2003 | Helsel et al. | 2002/0163484 A1 | 11/2002 | Furness, III et al. |
| 6,661,393 B2 | 12/2003 | Tegreene et al. | 2002/0167462 A1 | 11/2002 | Lewis et al. |
| 6,674,993 B1 | 1/2004 | Tarbouriech | 2002/0171776 A1 | 11/2002 | Tegreene et al. |
| 6,685,804 B1 | 2/2004 | Ikeda et al. | 2002/0171937 A1 | 11/2002 | Tegreene et al. |
| 6,687,034 B2 | 2/2004 | Wine et al. | 2003/0016187 A1 | 1/2003 | Melville et al. |
| 6,689,056 B1 | 2/2004 | Kilcoyne et al. | 2003/0030753 A1 | 2/2003 | Kondo et al. |
| 6,699,170 B1 | 3/2004 | Crocker et al. | 2003/0032143 A1 | 2/2003 | Neff et al. |
| 6,700,552 B2 | 3/2004 | Kollin et al. | 2003/0034709 A1 | 2/2003 | Jerman |
| 6,714,331 B2 | 3/2004 | Lewis et al. | 2003/0058190 A1 | 3/2003 | Lewis et al. |
| 6,734,835 B2 | 5/2004 | Tidwell et al. | 2003/0086172 A1 | 5/2003 | Urey |
| 6,736,511 B2 | 5/2004 | Plummer et al. | 2003/0092995 A1 | 5/2003 | Thompson |
| 6,741,884 B1 | 5/2004 | Freeman et al. | 2003/0130562 A1 | 7/2003 | Barbato et al. |
| 6,749,346 B1 | 6/2004 | Dickensheets et al. | 2003/0142934 A1 | 7/2003 | Pan et al. |
| 6,755,536 B2 | 6/2004 | Tegreene et al. | 2003/0159447 A1 | 8/2003 | Sergio et al. |
| 6,762,867 B2 | 7/2004 | Lippert et al. | 2003/0214460 A1 | 11/2003 | Kovacs |
| 6,768,588 B2 | 7/2004 | Urey | 2003/0216729 A1 | 11/2003 | Marchitto et al. |
| 6,771,001 B2 | 8/2004 | Mao et al. | 2004/0004585 A1 | 1/2004 | Brown et al. |
| 6,782,748 B2 | 8/2004 | Weber et al. | 2004/0057103 A1 | 3/2004 | Bernstein |

| | | |
|---|---|---|
| 2004/0075624 A1 | 4/2004 | Tegreene et al. |
| 2004/0076390 A1 | 4/2004 | Dong Yang et al. |
| 2004/0085261 A1 | 5/2004 | Lewis et al. |
| 2004/0085617 A1 | 5/2004 | Helsel et al. |
| 2004/0087844 A1 | 5/2004 | Yen |
| 2004/0101822 A1 | 5/2004 | Wiesner et al. |
| 2004/0113059 A1 | 6/2004 | Kawano et al. |
| 2004/0118821 A1 | 6/2004 | Han et al. |
| 2004/0119004 A1 | 6/2004 | Wine et al. |
| 2004/0122328 A1 | 6/2004 | Wang et al. |
| 2004/0133786 A1 | 7/2004 | Tarbouriech |
| 2004/0151466 A1 | 8/2004 | Crossman-Bosworth et al. |
| 2004/0155186 A1 | 8/2004 | Nestorovic et al. |
| 2004/0155834 A1 | 8/2004 | Wit et al. |
| 2004/0179254 A1 | 9/2004 | Lewis et al. |
| 2004/0196518 A1 | 10/2004 | Wine et al. |
| 2004/0223202 A1 | 11/2004 | Lippert et al. |
| 2004/0225222 A1 | 11/2004 | Zeng et al. |
| 2004/0236371 A1 | 11/2004 | McNally-Heintzelman et al. |
| 2004/0240866 A1 | 12/2004 | Ramsbottom |
| 2004/0252377 A1 | 12/2004 | Urey |
| 2004/0254474 A1 | 12/2004 | Seibel et al. |
| 2005/0010787 A1 | 1/2005 | Tarbouriech |
| 2005/0014995 A1 | 1/2005 | Amundson et al. |
| 2005/0020877 A1 | 1/2005 | Ishihara et al. |
| 2005/0020926 A1* | 1/2005 | Wiklof et al. ............... 600/476 |
| 2005/0023356 A1 | 2/2005 | Wiklof et al. |
| 2005/0030305 A1 | 2/2005 | Brown et al. |
| 2005/0038322 A1 | 2/2005 | Banik |
| 2005/0116051 A1 | 6/2005 | Lewis et al. |
| 2005/0162762 A1 | 7/2005 | Novak |
| 2005/0187441 A1 | 8/2005 | Kawasaki et al. |
| 2005/0203343 A1* | 9/2005 | Kang et al. ................. 600/160 |
| 2005/0240147 A1 | 10/2005 | Makower et al. |
| 2006/0010985 A1 | 1/2006 | Schneider |
| 2006/0084867 A1 | 4/2006 | Tremblay et al. |
| 2006/0164330 A1 | 7/2006 | Bright et al. |
| 2006/0183246 A1 | 8/2006 | Wiesner et al. |
| 2006/0195014 A1 | 8/2006 | Seibel et al. |
| 2006/0238774 A1 | 10/2006 | Lindner et al. |
| 2006/0245971 A1 | 11/2006 | Burns et al. |
| 2006/0284790 A1 | 12/2006 | Tegreene et al. |
| 2007/0038119 A1 | 2/2007 | Chen et al. |
| 2007/0046778 A1 | 3/2007 | Ishihara et al. |
| 2007/0135770 A1 | 6/2007 | Hunt et al. |
| 2007/0156021 A1 | 7/2007 | Morse et al. |
| 2007/0161876 A1 | 7/2007 | Bambot et al. |
| 2007/0162093 A1 | 7/2007 | Porter et al. |
| 2007/0167681 A1 | 7/2007 | Gill et al. |
| 2007/0173707 A1 | 7/2007 | Mitra |
| 2007/0179366 A1 | 8/2007 | Pewzner et al. |
| 2007/0197874 A1 | 8/2007 | Ishihara |
| 2007/0197875 A1 | 8/2007 | Osaka |
| 2007/0203413 A1 | 8/2007 | Frangioni |
| 2007/0213588 A1 | 9/2007 | Morishita et al. |
| 2007/0213618 A1 | 9/2007 | Li et al. |
| 2007/0225695 A1 | 9/2007 | Mayer et al. |
| 2007/0238930 A1 | 10/2007 | Wiklof et al. |
| 2007/0244365 A1 | 10/2007 | Wiklof |
| 2007/0260121 A1 | 11/2007 | Bakos et al. |
| 2007/0260273 A1 | 11/2007 | Cropper et al. |
| 2008/0058629 A1 | 3/2008 | Seibel et al. |

FOREIGN PATENT DOCUMENTS

| | | |
|---|---|---|
| EP | 1139141 | 10/2001 |
| EP | 1716802 | 11/2006 |
| EP | 1747751 | 1/2007 |
| EP | 1797813 | 6/2007 |
| JP | 2007-244590 | 9/2007 |
| JP | 2007-244680 | 9/2007 |
| WO | WO 98/13720 | 4/1998 |
| WO | WO 99/18456 | 4/1999 |
| WO | 99/58930 | 11/1999 |
| WO | 00/13210 | 3/2000 |
| WO | 01/10322 | 2/2001 |
| WO | 01/60274 | 8/2001 |
| WO | 02/062239 | 8/2002 |
| WO | WO 03/069380 | 8/2003 |
| WO | 03/088643 | 10/2003 |
| WO | 03/098918 | 11/2003 |
| WO | 03/101287 | 11/2003 |
| WO | 2006/020605 | 2/2006 |
| WO | WO 2006/049787 | 5/2006 |
| WO | WO 2006/055733 | 5/2006 |
| WO | 2007/041542 | 4/2007 |
| WO | 2007/070831 | 6/2007 |
| WO | WO 2007/067163 | 6/2007 |
| WO | WO 2007/084915 | 7/2007 |

OTHER PUBLICATIONS

Lewis, J.R. et al., "Scanned beam medical imager," MOEMS Display and Imaging Systems II, Proceedings of SPIE vol. 5348, pp. 40-51 (2004).

James, R. et al., "Update on MEMS-based Scanned Beam Imager" (date of first publication unknown).

Wiklof, C., "Display technology spawns laser camera," Laser Focus World (Dec. 2004).

"Press Information—Phillips' Fluid Lenses Bring Things into Focus," http://www.newscenter.philips.com (Mar. 3, 2004).

Lettice, J., "The $5 'no moving parts' fluid zoom lens—twice," The Register (Mar. 15, 2004).

"Volcano Products—IVUS Imaging Visions® PV018," http://www.volcanotherapeutics.com (date of first publication unknown).

Barhoum, E.S. et al., "Optical modeling of an ultrathin scanning fiber endoscope, a preliminary study of confocal versus non-confocal detection," Optics Express, vol. 13, No. 19, pp. 7548-7652 (Sep. 19, 2005).

"Crystalplex Technology—PlxBead™ Superior Qualities," http:www.crystalplex.com (date of first publication unknown).

"Microvision [illuminating information] Products/Overview, Corporate Overview Presentation 2006" (2006).

"Holographic Beam Combiner for Ladar, Printer, Fiber Optics, and Cancer Treatment," by Digital Optics Technologies, Inc., http://www.mdatechnology.net (date of first publication unknown).

Brown, D.M., Abstract from SPIE Digital Library for "High-power laser diode beam combiner," Optical Engineering, vol. 42, Issue 11 (2003).

Literature entitled "All fiber beam combiner from Point Source" (Oct. 13, 2006).

"Custom Polarzing Cube Beamsplitters," from GlobalSpec The Engineering Search Engine, http://www.globalspec.com (date of first publication unknown).

Literature entitled "Dallas Semiconductor MAXIM—Visible-Laser Driver has Digitally Controlled Power Modulation," by Maxim Integrated Products, http://www.maxim-ic.com (Jul. 1, 2001).

"SCAN Mode Strategies for SCUBA-2" (May 25, 2005).

Seifert, M. et al., "High Power Diode Laser Beam Scanning in Multi-Kilowatt Range," Proceedings of the 23rd International Congress on Applications of Lasers and Electro-Optics (2004).

Jutzi, B. et al., "Sub-Pixel Edge Localization Based on Laser Waveform Analysis," ISPRS WG III/3, III/4, V/3 Workshop "Laser scanning 2005," Enschede, the Netherlands (Sep. 12-14, 2005).

"Bladeless Trocars," by Johnson & Johnson, http://www.jnjgateway.com (date of first publication unknown).

Yeh, R. et al., "Microelectromechanical Components for Articulated Microrobots" (date of first publication unknown).

Xu, Q. et al., "Micrometre-scale silicon electro-optic modulator," Nature, vol. 435, pp. 325-327 (May 19, 2005).

Park, H. et al., "Development of Double-Sided Silicon Strip Position Sensor," 2005 IEEE Nuclear Science Symposium Conference Record, pp. 781-785 (2005).

Hammond, S.W., "Architecture and Operation of a Systolic Sparse Matrix Engine," Proceedings of the 3rd SIAM Conference on Parallel Processing for Scientific Computing, pp. 419-423 (1987).

PCT, International Search Report, PCT/US2008/056589 (Jul. 30, 2008).
PCT, International Search Report, PCT/US2008/059231 (Jul. 4, 2008).
PCT, International Search Report, PCT/US2007/087923 (May 21, 2008).
PCT, International Search Report, PCT/US2008/056596 (Jun. 23, 2008).
PCT, International Search Report, PCT/US2008/059235 (Jul. 14, 2008).
PCT, International Search Report, PCT/US2007/087930 (Jul. 3, 2008).
PCT, International Search Report, PCT/US2008/051274 (Jul. 18, 2008).
International Search Report issued regarding International Application No. PCT/US2007/078868 (Mar. 28, 2008).
PCT, International Search Report, PCT/US2008/066552 (Oct. 23, 2008).
Invitation to Pay Additional Fees with Partial International Search Report, PCT/US2008/074275 (Jan. 16, 2009).
Invitation to Pay Additional Fees with Partial International Search Report, PCT/US2008/074273 (Dec. 30, 2008).

* cited by examiner

SCANNING BEAM IMAGING WITH ADJUSTABLE DETECTOR SENSITIVITY OR GAIN

FIELD OF INVENTION

This invention relates to improvements in scanning beam assemblies of the type that employ an oscillating reflector to control the scanning beam and a detector to detect the beam on a point by point basis as it is reflected from the field of view (FOV). The invention further related to scanning beam imaging systems incorporating such scanning assemblies and to corresponding improvements in devices, and still more particularly medical devices, including such an assembly.

BACKGROUND OF THE INVENTION

Figure 1:
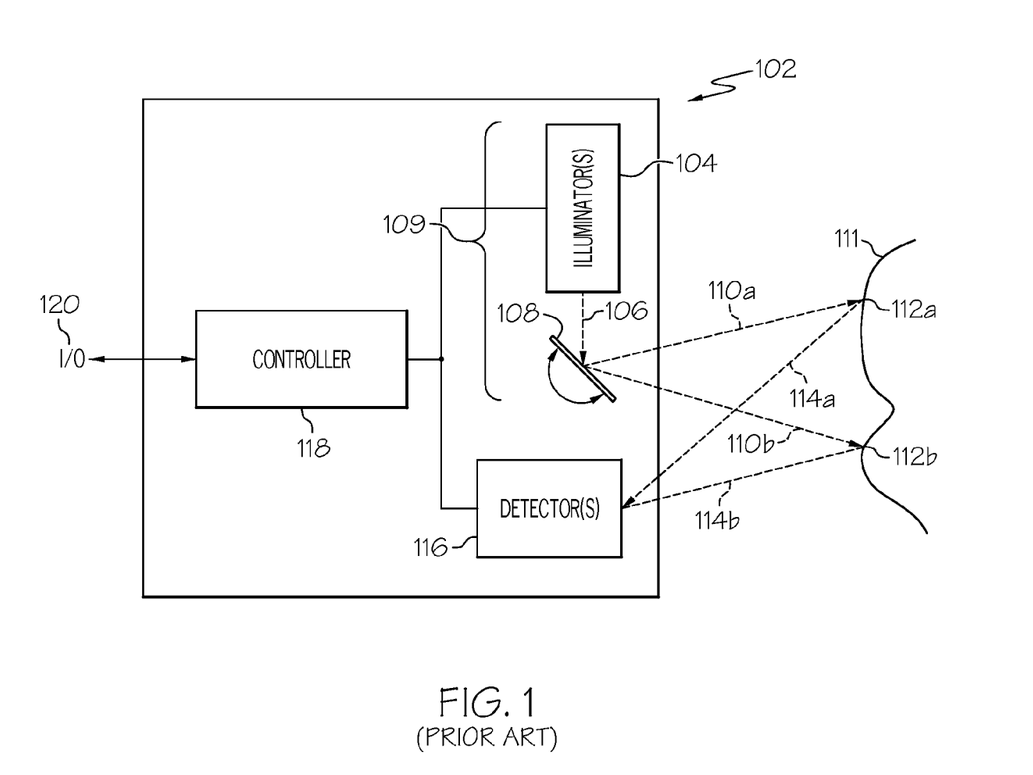
FIG. 1 is a schematic illustration of a scanning beam imager known in the art from Published application 2005/0020926A1.

U.S. Published application 2005/0020926A1 discloses a scanning beam imager which is reproduced in FIG. 1 herein. This imager can be used in applications in which cameras have been used in the past. In particular it can be used in medical devices such as video endoscopes, laparoscopes, etc.

FIG. 1 shows a block diagram of one example of a scanned beam imager 102. An illuminator 104 creates a first beam of light 106. A scanner 108 deflects the first beam of light across a field-of-view (FOV) to produce a second scanned beam of light 110, shown in two positions 110a and 110b. The scanned beam of light 110 sequentially illuminates spots 112 in the FOV, shown as positions 112a and 112b, corresponding to beam positions 110a and 110b, respectively. While the beam 110 illuminates the spots 112, the illuminating light beam 110 is reflected, absorbed, scattered, refracted, or otherwise affected by the object or material in the FOV to produce scattered light energy. A portion of the scattered light energy 114, shown emanating from spot positions 112a and 112b as scattered energy rays 114a and 114b, respectively, travels to one or more detectors 116 that receive the light and produce electrical signals corresponding to the amount of light energy received. Image information is provided as an array of data, where each location in the array corresponds to a position in the scan pattern. The electrical signals drive an image processor 118 that builds up a digital image and transmits it for further processing, decoding, archiving, printing, display, or other treatment or use via interface 120.

Illuminator 104 may include multiple emitters such as, for instance, light emitting diodes (LEDs), lasers, thermal sources, arc sources, fluorescent sources, gas discharge sources, or other types of illuminators. In some embodiments, illuminator 104 comprises a red laser diode having a wavelength of approximately 635 to 670 nanometers (nm). In another embodiment, illuminator 104 comprises three lasers: a red diode laser, a green diode-pumped solid state (DPSS) laser, and a blue DPSS laser at approximately 635 nm, 532 nm, and 473 nm, respectively. Light source 104 may include, in the case of multiple emitters, beam combining optics to combine some or all of the emitters into a single beam. Light source 104 may also include beam-shaping optics such as one or more collimating lenses and/or apertures. Additionally, while the wavelengths described in the previous embodiments have been in the optically visible range, other wavelengths may be within the scope of the invention. Light beam 106, while illustrated as a single beam, may comprise a plurality of beams converging on a single scanner 108 or onto separate scanners 108.

In a resonant scanning beam imager (SBI), the scanning reflector or reflectors oscillate such that their angular deflection in time is approximately a sinusoid. One example of these scanners employs a MEMS scanner capable of deflection at a frequency near its natural mechanical resonant frequencies. This frequency is determined by the suspension stiffness, and the moment of inertia of the MEMS device incorporating the reflector and other factors such as temperature. This mechanical resonant frequency is referred to as the "fundamental frequency." Motion can be sustained with little energy and the devices can be made robust when they are operated at or near the fundamental frequency. In one example, a MEMS scanner oscillates about two orthogonal scan axes. In another example, one axis is operated near resonance while the other is operated substantially off resonance. Such a case would include, for example, the non-resonant axis being driven to achieve a triangular, or a saw-tooth angular deflection profile as is commonly utilized in cathode ray tube (CRT)-based video display devices. In such cases, there are additional demands on the driving circuit, as it must apply force throughout the scan excursion to enforce the desired angular deflection profile, as compared to the resonant scan where a small amount of force applied for a small part of the cycle may suffice to maintain its sinusoidal angular deflection profile.

Figure 2:
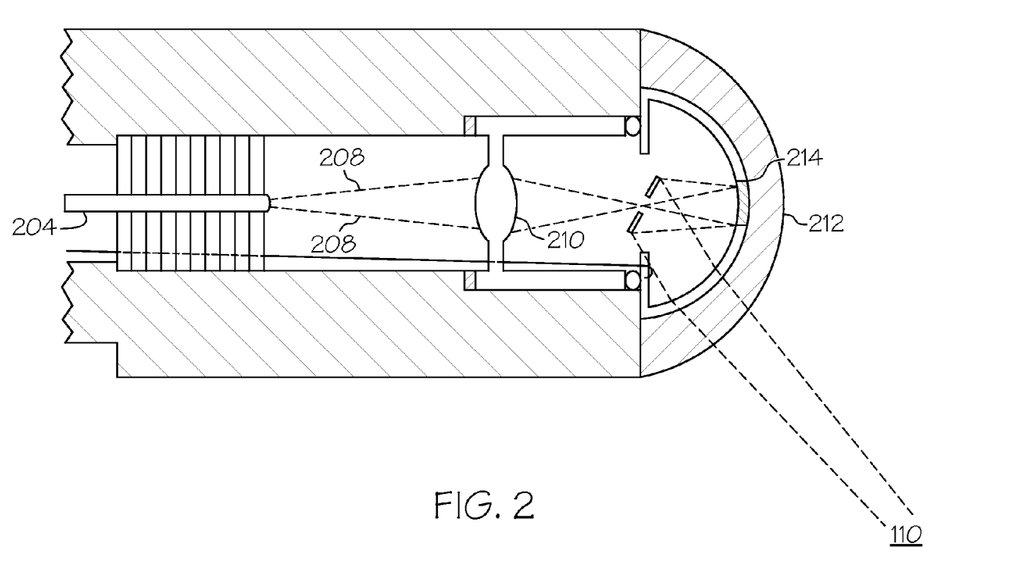
FIG. 2 is a schematic diagram of a optical system employing a concave lens with a central reflector dot.

As illustrated in FIG. 2, in one embodiment the scanner employs a concave objective lens or dome 212 having a partially reflective surface 214. The area of this surface will be appropriate for the medical application and the device design. In one embodiment it may be about 8 mm or less in diameter and in another embodiment it may be about 100-300 micron in diameter. This reflective surface may be integral to the dome 212, located centrally on the lens surface, as shown in FIG. 2 or it may be suspended or mounted on the incident side of the dome. The dome 212 has optical power and shapes the scanned beam 110 as it passes through the dome. In one embodiment, in order to view the areas directly behind the surface 214, the surface 214 is a material that is only partially reflective. The beam 208 emitted from the optical fiber 204 is directed to the reflector 214 via the shaping optic 210. The major portion (note FIG. 3) of the beam radiation is reflected by the reflector to the oscillating reflector 108 and from reflector 108 into the FOV as scanned beam 110. A smaller portion of the beam passes through the surface 214. This "leakage" radiation passing through the surface 14 is reflected from the field of view (FOV). This light is diffuse and when the reflector is not directing light/radiation through the surface 214, the light is not correlated with the point in the FOV that the scanner is interrogating. In this case it constitutes a source of noise that negatively impacts the SNR (signal to noise ratio). As shown in FIG. 1, a portion of the radiation reflected/scattered from the FOV, travels to one or more detectors 116 that receive the light and produce electrical signals corresponding to the amount of light energy received.

Figure 3:
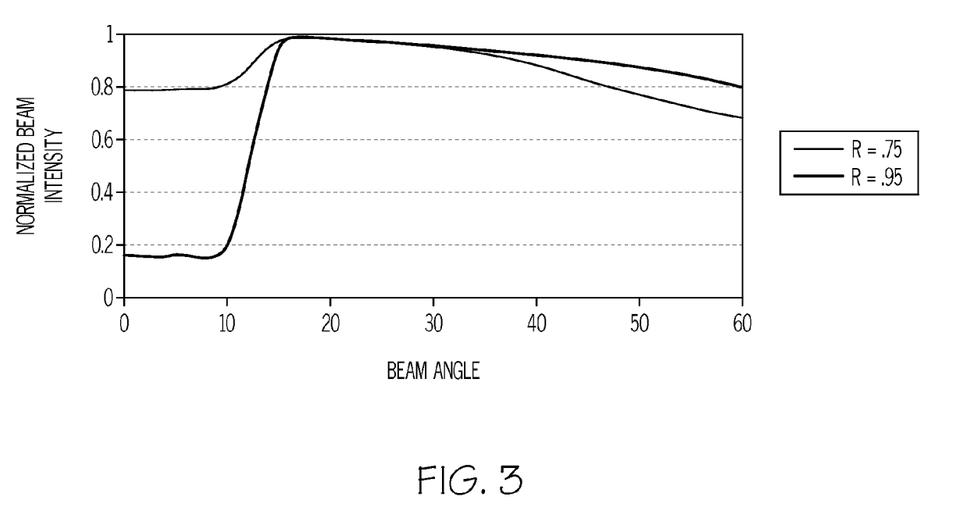
FIG. 3 is a graph of normalized detected beam intensity versus beam angle for one example of a dome incorporating a partially reflective area 214 having reflection coefficients (R) of 0.75 and 0.95 (taking into account typical detector design and efficiency).

FIG. 3 is a graph of normalized detected beam intensity versus beam angle for an integral central reflective surface or "dot" reflector of the type illustrated in FIG. 2 having reflection coefficients of 0.75 and 0.95 respectively. FIG. 3 shows that less light is transmitted to and then returned to the detectors from the scene in the portion of the FOV covered by the projection of the reflective dot. For a reflective dot having a reflection coefficient of 0.75, 80% of the beam is reflected whereas for a reflective dot having a reflection coefficient of 0.95, less than 20% of the beam is reflected. Regardless of the reflection coefficient, as the angle at which the scanned beam is defected from the scanning reflector increases, e.g., at beam angles greater than about 25°, the beam intensity decreases, thereby also reducing the SNR of these wider angle beams.

SUMMARY

In accordance with this disclosure, scanning beam imagers are provided with a detector having adjustable sensitivity and/or gain, and a controller that adjusts the gain and/or the sensitivity of the detector to compensate for the effects described above. In more particular embodiments, the detector may include a controllable power source and/or a variable gain amplifier.

One embodiment provides for a timed increase in the gain of the detector during those periods of time in which the scanned beam is at its wider angles. Another embodiment provides for a timed increase in the sensitivity of the detector during those periods of time in which the scanned beam intersects the partially reflective surface. Another embodiment provides both functions.

A further embodiment of the invention is an endoscope or laproscope that employs an imager that is constructed and operated as described herein.

Another embodiment is a method for operating a scanning beam imager as described herein.

DETAILED DESCRIPTION

Before explaining the several embodiments of the present invention in detail, it should be noted that each embodiment is not limited in its application or use to the details of construction and arrangement of parts and steps illustrated in the accompanying drawings and description. The illustrative embodiments of the invention may be implemented or incorporated in other embodiments, variations and modifications, and may be practiced or carried out in various ways. Furthermore, unless otherwise indicated, the terms and expressions employed herein have been chosen for the purpose of describing the illustrative embodiments of the present invention for the convenience of the reader and are not for the purpose of limiting the invention.

It is further understood that any one or more of the following-described embodiments, examples, etc. can be combined with any one or more of the other following-described embodiments, examples, etc.

In accordance with certain embodiments of the invention, scanner 108 is a MEMS scanner. MEMS scanners can be designed and fabricated using any of the techniques known in the art as summarized in the following references: U.S. Pat. Nos. 6,140,979, 6,245,590, 6,285,489, 6,331,909, 6,362,912, 6,384,406, 6,433,907, 6,512,622, 6,515,278, 6,515,781, and/or 6,525,310, all hereby incorporated by reference. In one embodiment, the scanner may be a magnetically resonant scanner as described in U.S. Pat. No. 6,151,167 of Melville, or a micromachined scanner as described in U.S. Pat. No. 6,245,590 to Wine et al.

In accordance with one embodiment of the invention, a scanning beam assembly of the type described in U.S. Published application 2005/0020926A1 is used.

The assembly is constructed with a detector having adjustable gain or sensitivity or both. In one embodiment, the detector may include a detector element that is coupled with a means for adjusting the signal from the detector element such as a variable gain amplifier. In another embodiment, the detector may include a detector element that is coupled to a controllable power source. In still another embodiment, the detector may include a detector element that is coupled both to a controllable power source and a variable gain or voltage controlled amplifier. Representative examples of detector elements useful in certain embodiments of the invention are photomultiplier tubes (PMT's), charge coupled devices (CCD's), photodiodes, etc.

Figure 4:
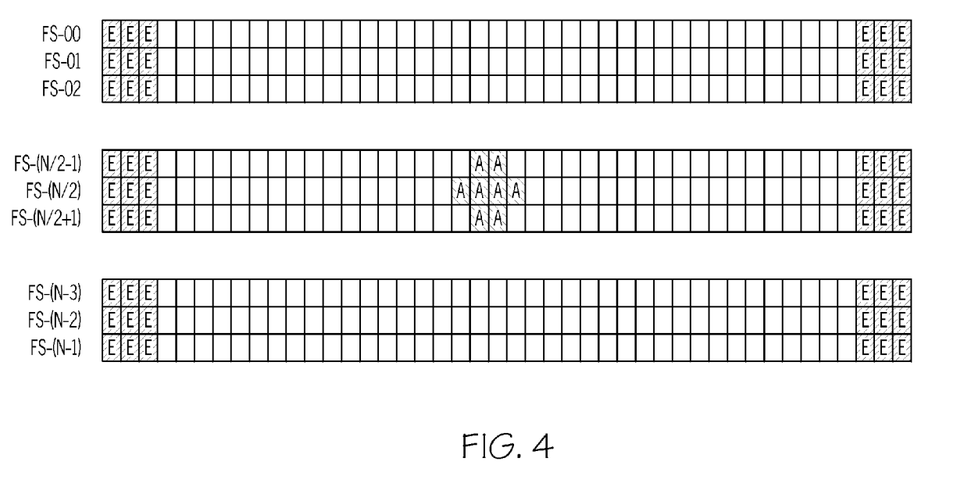
FIG. 4 is one non-limiting example of a timing diagram for adjusting gain and/or detector sensitivity as described herein.

In accordance with one embodiment of the invention, the detector gain and/or sensitivity is adjusted to compensate for those areas in the FOV in which the SNR is low. More particularly, FIG. 4 is a chart showing detector sample timing wherein the times/positions at which the scanned beam intersects the partial reflector (A) and the wider beam angles (E) are respectively designated on Cartesian coordinates. In accordance with one embodiment, the assembly includes a controller that increases the sensitivity of the detector to compensate for the SNR when the beam intersects areas A. In certain embodiments, the scanning beam assembly may not include the partial reflector 214 and hence areas A will not be present in the field of view. For example, those skilled in the art will recognize that optical paths can be designed in which the beam optics are not located within the field of view thereby obviating the need for the partial reflector 214. In these embodiments, detector adjustments would not be necessary to compensate for the noise levels associated with the partial reflector 214.

In accordance with one embodiment, the assembly includes a controller that increases the sensitivity of the detector when the beam intersects areas A. In accordance with another embodiment, the assembly includes a controller that increases the gain of the detector when the beam intersects areas E. In one embodiment of the invention, areas E correspond to beam excursions of greater than about 25 degrees and in a more particular embodiment, areas E correspond to excursions greater than about 40 degrees and in a still more particular embodiment, areas E correspond to beam excursions greater than about 50 degrees. More particularly, with regard to areas E, when the scanner in includes a partially reflective surface 214, the beam angle at which it may be advantageous to increase the gain will be a function of the reflection coefficient of surface 214 as is apparent from FIG. 3. In one embodiment using a reflective surface 214 having a reflective coefficient of 75%, increasing the gain may not be required until the beam excursions is greater than 40° and in another embodiment using a reflective surface having a reflective coefficient of 95%, increasing the gain may not be required until beam excursion is greater than 50°. In still another embodiment, the controller adjusts the gain and/or sensitivity of the detector when the beam interrogates points in areas A and areas E.

Figure 5:
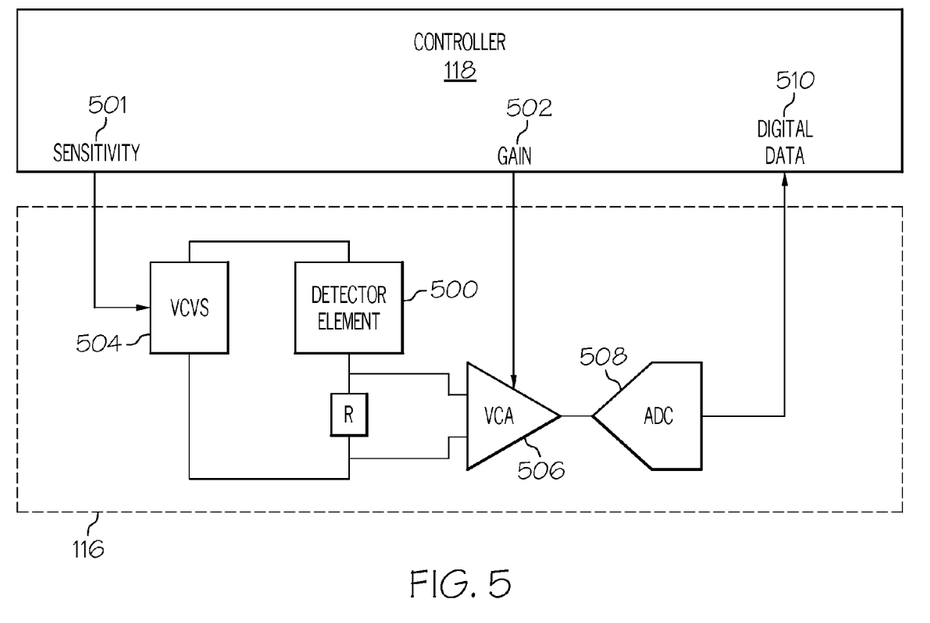
FIG. 5 is a control diagram showing processes for controlling detector gain and sensitivity in accordance with one embodiment of the invention.

FIG. 5 is a control diagram illustrating one embodiment in which the controller 118 is operatively connected to the detector 116 to modify the detector gain through control ports labeled Sensitivity 501 and Gain 502. The detector 116 includes a detector element 500 that generates a signal in response to radiation. In the illustrated embodiment, the sensitivity port 502 is operably connected to a controllable power source such as a Voltage Controlled Voltage Source (VCVS 504). In one embodiment the sensitivity control port 502 employs analog signaling. In another embodiment, the sensitivity control port 502 employs digital signaling. The gain port 501 is operably connected to a voltage controlled amplifier (VCA 506). In one embodiment, the gain control port 501 employs analog signaling. In another embodiment, the gain control port 501 employs digital signaling. Based on the current scan path, controller 118 apportions detector gain settings to the sensitivity and gain control ports. The controller 118 must be able to update settings during each detector sample period or during a small number of temporally contiguous sample periods. In one embodiment, a standard lookup table suitably sized to match the number of detector samples taken per fame is used to drive the sensitivity and gain ports 501 and 502. The lookup table could be pre-calculated for each point in the FOV. To account for manufacturing tolerances, the look-up tables may be customized for each interchangeable scanning mirror device. The output from the VCA 506 in the illustrated embodiment is processed through an analog-to-digital converter 508 to provide the digital output 510. In one embodiment, the output 510 may be processed by an image processor to produce an image of the field of view. In another embodiment, the output 510 is not necessarily processed to form an image but may be fed to a controller to control directly a therapeutic treatment such as a laser. See, for example, U.S. application Ser. No. 11/615,140 (Attorney's docket END5904).

As one non-limiting illustration of the control function where the partially reflective area has R=0.75, 80% of the illumination incident on the scene is captured by the detector system for a central beam (angle=0). To compensate, the effective gain of the detector system can be adjusted to 1.25 (e.g., 1/0.8) in the areas designated A in FIG. 4. On the other hand, the edge of the FOV, for example the areas E in FIG. 4, both reflectivities (R=0.75 and R=0.90) yield intensities of about 70%. For this case the gain can be set to about 1.4 (e.g., 1/0.70).

There are, according to FIG. 5, two controls for gain in the system. One control referred to as Sensitivity, the other referred to as Gain. In a particular detector, an APD or Avalanche Photo Diode, sensitivity can be controlled by the applied bias voltage (controlled by the VCVS in FIG. 5). This type of gain control is relatively slow. In one embodiment, this control can best be used to adjust the gain or "brightness level" of the overall image, not the areas A and E under discussion. Another method to control the gain is to provide a Voltage Controlled Amplifier (sometimes referred to as a Variable Gain Amplifier) just prior to sending the detector output to the A/D converter (ADC in FIG. 5). These circuits have extremely rapid response and can be used to change the gain many times during a single oscillation of the scanning mirror.

It will be understood that the foregoing description is provided by way of example, and that other modifications and variations there may be made by persons skilled in the art without departing from the scope and spirit of the invention as defined by the appended claims.

What is claimed is:

1. A scanning beam assembly comprising:
 a beam generator to generate a first beam of radiation,
 an oscillating reflector configured to deflect the first beam of radiation at varying angles of excursion to yield a scanned beam that scans a field of view,
 an optical detector that detects light reflected from the field of view, the detector including at least one of an adjustable gain and adjustable sensitivity, and
 a controller programmable to vary the gain and/or sensitivity of the detector depending on the angle of excursions,
 wherein the beam assembly includes a partially reflective surface that reflects the first beam of radiation from the beam generator to the oscillating reflector and wherein the controller is programmed to increase the sensitivity of the detector when the scanned beam intersects the partially reflective surface for all distances from the oscillating reflector to illuminated spots in the field of view.

2. The scanning beam assembly of claim 1 wherein the controller is programmed to increase the gain of the detector when the scanned beam is reflected at predetermined wide angles of excursion within the field of view for all distances from the oscillating reflector to illuminated spots in the field of view.

3. The scanning beam assembly of claim 2 wherein the controller is programmed to increase the gain of the detector when the scanned beam is reflected at an angle greater than about 25 degrees.

4. The scanning beam assembly of claim 1 wherein the beam assembly includes a partially reflective surface that reflects the first beam of radiation from the beam generator to the oscillating reflector and wherein the controller is programmed to increase the gain of the detector when the scanned beam is reflected at predetermined wide angles of excursion for all distances from the oscillating reflector to illuminated spots in the field of view and to increase the sensitivity of the detector when the scanned beam intersects the partially reflective surface for all distances from the oscillating reflector to illuminated spots in the field of view.

5. The scanning beam assembly of claim 4 wherein the controller is programmed to increase the gain of the detector when the scanned beam is reflected at an angle greater than about 25 degrees.

6. The scanning beam assembly of claim 1 wherein the detector includes a detector element and a means for adjusting the gain or sensitivity of the detector.

7. The scanning beam assembly of claim 6 wherein the means for adjusting the gain or sensitivity of the detector is selected from the group consisting of a variable gain amplifier, a controllable power source, or a combination thereof.

8. The scanning beam assembly of claim 7 wherein the detector includes a detector element selected from the group consisting of a PMT, CCD, photodiode, an avalanche photodiode, and amorphous silicon.

9. The scanning beam assembly of claim 6 wherein the oscillating reflector includes a MEMS scanner and a concave optic.

10. The scanning beam assembly of claim 9 wherein the assembly forms part of a scanning beam imager or a scanning beam illuminator.

11. The scanning beam assembly of claim 10 wherein the assembly includes a partially reflective surface that reflects the beam of radiation from the beam generator to the oscillating reflector and the controller is programmed to increase the sensitivity of the detector when the scanned beam intersects the partially reflective surface for all distances from the oscillating reflector to illuminated spots in the field of view.

12. The scanning beam assembly of claim 11 wherein the controller is programmed to increase the gain of the detector when the scanned beam is reflected at angles greater than about 25 degrees.

13. A scanned beam endoscope comprising:
an endoscope, and
a scanning beam assembly including:
    a beam generator to generate a first beam of radiation,
    an oscillating reflector configured to deflect the first beam of radiation at varying angles of excursion to yield a scanned beam that scans a field of view,
    an optical detector that detects light reflected from the field of view, the detector including at least one of an adjustable gain and sensitivity, and
    a controller programmable to vary the gain and/or sensitivity of the detector depending on the angle of excursion,
    wherein the beam assembly includes a partially reflective surface that reflects the first beam of radiation from the beam generator to the oscillating reflector and wherein the controller is programmed to increase the sensitivity of the detector when the scanned beam intersects the partially reflective surface for all distances from the oscillating reflector to illuminated spots in the field of view.

14. The endoscope of claim 13 wherein the controller is programmed to increase the gain of the detector when the scanned beam is reflected at predetermined wide angles of excursion for all distances from the oscillating reflector to illuminated spots in the field of view.

15. The endoscope of claim 14 the controller is programmed to increase the gain of the detector when the scanned beam is reflected at an angle greater than about 20 degrees.

16. The endoscope of claim 13 wherein the beam assembly includes a partially reflective surface that reflects the first beam of radiation from the beam generator to the oscillating reflector and wherein the controller is programmed to increase the gain of the detector when the scanned beam is reflected at predetermined wide angles of excursion for all distances from the oscillating reflector to illuminated spots in the field of view and to increase the sensitivity of the detector when the scanned beam intersects the partially reflective surface for all distances from the oscillating reflector to illuminated spots in the field of view.

17. The endoscope of claim 13 wherein the detector includes a detector element and a means for adjusting the gain or sensitivity of the detector.

18. The endoscope of claim 17 wherein the means for adjusting the gain or sensitivity of the detector is selected from the group consisting of a variable gain amplifier, a controllable power source, or a combination thereof.

19. A scanning beam assembly comprising:
a beam generator to generate a first beam of radiation,
an oscillating reflector configured to deflect the first beam of radiation at varying angles of excursion to yield a scanned beam that scans a field of view,
an optical detector that detects light reflected from the field of view, the detector including at least one of an adjustable gain and adjustable sensitivity, and
a controller programmable to vary the gain and/or sensitivity of the detector depending on the angle of excursion, wherein the controller is programmed to increase the gain of the detector when the scanned beam is reflected at an angle greater than about 25 degrees, and
vherein the beam assembly includes a partially reflective surface that reflects the first beam of radiation from the beam generator to the oscillating reflector and wherein the controller is programmed to increase the gain of the detector when the scanned beam is reflected at predetermined wide angles of excursion for all distances from the oscillating reflector to illuminated spots in the field of view and to increase the sensitivity of the detector when the scanned beam intersects the partially reflective surface for all distances from the oscillating reflector to illuminated spots in the field of view.

* * * * *